United States Patent
Reichel

(10) Patent No.: US 9,757,089 B2
(45) Date of Patent: Sep. 12, 2017

(54) ROTATING UNIT WITH A DEVICE FOR WIRELESS DATA TRANSMISSION BETWEEN TWO PARTS MOVABLE RELATIVE TO ONE ANOTHER, AND METHOD FOR WIRELESS DATA TRANSMISSION BETWEEN TWO PARTS MOVABLE RELATIVE TO ONE ANOTHER

(71) Applicant: Siemens Aktiengesellschaft, Munich (DE)

(72) Inventor: Werner Reichel, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 254 days.

(21) Appl. No.: 14/447,832

(22) Filed: Jul. 31, 2014

(65) Prior Publication Data
US 2015/0036791 A1 Feb. 5, 2015

(30) Foreign Application Priority Data

Jul. 31, 2013 (DE) .......................... 10 2013 215 045

(51) Int. Cl.
*A61B 6/00* (2006.01)
*A61B 6/03* (2006.01)
*H04B 7/26* (2006.01)

(52) U.S. Cl.
CPC ................. *A61B 6/56* (2013.01); *A61B 6/03* (2013.01); *A61B 6/032* (2013.01); *H04B 7/26* (2013.01)

(58) Field of Classification Search
CPC .............. A61B 6/563; A61B 6/53; A61B 6/56
See application file for complete search history.

(56) References Cited

U.S. PATENT DOCUMENTS

| | | | | |
|---|---|---|---|---|
| 2007/0035883 | A1* | 2/2007 | Katcha | A61B 6/56 360/281.8 |
| 2007/0040635 | A1* | 2/2007 | Popescu | A61B 6/035 333/261 |

(Continued)

FOREIGN PATENT DOCUMENTS

| | | |
|---|---|---|
| EP | 0 179 413 A1 | 10/1985 |
| WO | 01/86750 A1 | 11/2001 |
| WO | WO-2013/100274 A1 | 7/2013 |

*Primary Examiner* — David J Makiya
*Assistant Examiner* — Dani Fox
(74) *Attorney, Agent, or Firm* — Schiff Hardin LLP

(57) ABSTRACT

In a method and a device for wireless data transmission between two parts of a medical imaging device that are moving relative to one another, at least: a first communication device has at least one transmission unit to transmit at least one radio-frequency signal, a second communication device has at least one reception unit to receive at last one radio-frequency signal, and the first and second communication devices are arranged at the different parts of the rotating unit. A directional coupler has at least two radio-frequency conductors; with one of the radio-frequency conductors being connected at one end thereof with the first communication device, and the other end thereof is terminated with a real resistor. The second radio-frequency conductor is connected with the second communication device. One of the radio-frequency conductors extends annularly at least around the entire circumference of one of the two parts of the rotating unit that are movable relative to one another, while the other radio-frequency conductor is arranged on at least a portion of the circumference of the other part of the rotating unit; such that a constant power is extracted from the radio-frequency conductor connected with the communication device having at least one transmission unit.

16 Claims, 2 Drawing Sheets

(56) References Cited

U.S. PATENT DOCUMENTS

| | | | |
|---|---|---|---|
| 2008/0272296 A1* | 11/2008 | Frach | A61B 6/56 250/306 |
| 2008/0279302 A1 | 11/2008 | Granger et al. | |
| 2010/0310039 A1 | 12/2010 | Lindorfer | |
| 2011/0069819 A1* | 3/2011 | Urban | A61B 6/547 378/197 |

* cited by examiner

ROTATING UNIT WITH A DEVICE FOR WIRELESS DATA TRANSMISSION BETWEEN TWO PARTS MOVABLE RELATIVE TO ONE ANOTHER, AND METHOD FOR WIRELESS DATA TRANSMISSION BETWEEN TWO PARTS MOVABLE RELATIVE TO ONE ANOTHER

BACKGROUND OF THE INVENTION

Field of the Invention

The present invention concerns a rotating unit having two parts that are movable relative to one another, and a device for wireless data transmission (transfer) between the parts that are movable relative to one another, as well as a method for wireless data transmission between two parts of a medical device (for example a medical imaging device, in particular a computed tomography apparatus) that are movable relative to one another.

Description of the Prior Art

Particularly in computed tomography apparatuses, solutions are known that enable data transmission between parts that are movable (in particular rotatable) relative to one another. Computed tomography apparatuses are essentially composed of a base or gantry (thus a stator) and a rotating part (thus a rotor) that has an acquisition system and that is rotated around a rotation axis of the base. Measurement and operating data—for example the control data from the controller to the acquisition system as well as the projection data or image data from the acquisition system to a reception unit—must be transmitted between the stationary part and the rotating part. The acquisition system is composed of at least an x-ray tube and a detector system.

For example, such a data transmission is realized using slip rings. Such slip rings enable data transmission via a galvanic coupling across mechanical components that are afflicted by wear. However, such a solution is proprietary, and therefore expensive. Moreover, the data transmission is characterized by a slow transfer rate.

Another possibility is to realize the data transmission via a capacitive coupling of bit flows. Compared with data transmission via slip rings, the data transfer rate is faster. However, such a transmission is also proprietary, and therefore is similarly expensive. Moreover, such a data transmission is unidirectional and lacks integrated data security. Therefore, two transmission systems are necessary, and the data security must be implemented at higher protocol layers using firmware, which is complicated and additionally expensive.

SUMMARY OF THE INVENTION

An object of the present invention to provide a device and method data transmission between two parts movable relative to one another—namely between two parts rotatable relative to one another, preferably between a rotor and a stator of an imaging device, such as between a stationary part and a rotating part of a computed tomography apparatus—in a more simple, cost-effective and secure manner than those described above.

A typical radio-frequency communication device normally has at least one transmitter and/or one receiver; a radio-frequency conductor, and an antenna. For the purpose of data communication between two parts movable relative to one another, such a communication device can be integrated into a different part, or can be attached to a different part of a medical device. In a computed tomography apparatus with a rotatable part and a stationary part, however, the propagation path of the radio-frequency signal continuously changes due to the rotation of the rotating part, so the amplitude of the signal to be transmitted likewise changes continuously. In particular if metal parts that move over time are present in the near field (which is the case in a computed tomography apparatus), the signal to be transmitted can even be completely obliterated due to shielding and/or interference. The use of radio-frequency signals as a communication medium between a rotating part and a stationary part (in particular of a computed tomography apparatus) that are transmitted wirelessly by a radio-frequency communication device having an antenna therefore is generally not successful due to the fact that the transmission path between the antennas is not stable enough to ensure the transmission of security-critical control data between the parts (in particular of a computed tomography apparatus) that are movable relative to one another.

In this context, the invention is based on the insight that, for a radio-frequency communication device having an antenna, a constant radio-frequency field always forms along the radio-frequency conductor insofar as the radio-frequency conductor is terminated with a real ohmic resistor instead of with an antenna. In this region (namely at the radio-frequency conductor) constant conditions therefore always predominate if the termination of the conductor takes place with a real and correct impedance. The invention is based on the further insight that in this region—thus along such a radio-frequency conductor that is terminated in such a real ohmic manner—the constant field can be accessed with the use of a directional coupler. This means that a constant power can be extracted given a real load at the conductor end of the radio-frequency conductor, independently of the point along the radio-frequency conductor at which the directional coupler is introduced. Furthermore, both injection and extraction can take place via the directional coupler.

The term "transmission unit" as used in the following means a device to provide and/or transmit a signal, such as a radio-frequency signal or a WLAN signal. The signal is preferably a radio-frequency signal, especially a WLAN signal, having a defined frequency or a defined frequency range. The term "reception unit" as used in the following means a device to receive a signal, such as a radio-frequency signal or a WLAN signal, having a defined frequency or a defined frequency range. The signal to be transmitted is preferably a radio-frequency signal, especially a WLAN signal, having a defined frequency or a defined frequency range. The term "communication device" as used in the following means a device designed to provide and transmit and/or receive a signal, such as a radio-frequency signal or a WLAN signal. Such a communication device has at least one transmission unit to provide a radio-frequency signal or a WLAN signal, of a defined frequency or a defined frequency range, and/or a reception unit to receive a radio-frequency signal or a WLAN signal, of a different or the same frequency or a different or the same frequency range. A signal with a defined frequency, or a signal with a defined frequency range, is a signal that has at least one signal component with a defined frequency, or multiple signal components that each have a defined frequency range is respectively associated therewith.

The invention concerns a rotating unit having two parts that are movable relative to one another and a device for wireless transmission of measurement data and/or operating data between the two parts that are movable relative to one another. The parts that are movable relative to one another are preferably designed to be able to rotate relative to one another. The two parts that are movable relative to one another are advantageously fashioned in the form of a stator and a rotor. The wireless data transmission of the measurement data and/or operating data occurs between the different parts of the rotating unit, for example with the rotor and the stator. The rotor is preferably fashioned as a rotatable part and the stator is advantageously fashioned as a stationary part of a medical imaging device, in particular a computed tomography apparatus. Such data include measurement data and/or operating data. The measurement data are image data, for example projection data that are used for image reconstruction. The operating data are control data that, for example, serve or can serve for control and/or status determination of the different components located on the movable parts. The device for wireless data transmission also has at least one first communication device having at least one transmission unit; at least one second communication device having at least one reception unit; and at least one directional coupler having at least two radio-frequency conductors. Furthermore, the transmission unit is designed to provide and/or transmit a radio-frequency signal and the receiver device is designed to receive a radio-frequency signal. A radio-frequency signal is an electric signal with a frequency in a range from approximately 1 MHz to approximately 300 GHz.

According to the invention, the first and second communication devices are respectively attached to a different part of the parts that are movable relative to one another, so data transmission can take place between the movable parts. For example, a first communication device having at least one transmission unit is attached to a first part (to a stator, for example) and a second communication device with at least one reception unit is attached to a second part (for example to a rotor). The device for wireless data transmission according to the invention also has at least one directional coupler having two radio-frequency conductors. One of the radio-frequency conductors of the directional coupler is connected at one end thereof with a first communication device, and the other radio-frequency conductor of the directional coupler is connected with the remaining communication device. According to the invention, at least the radio-frequency conductor that is connected with a communication device that has at least one transmission unit is furthermore terminated at the other end with a real ohmic resistor (thus is terminated with a real resistance). Given a suitable selection of the impedance of the terminating resistor, a constant radio-frequency field develops along the radio-frequency conductor. It is thereby enabled to extract a signal (that is present or is induced in the first radio-frequency conductor) with the second radio-frequency conductor of the directional coupler that is connected at one end thereof with the second communication device having a reception unit. A signal can thereby be at least partially transmitted from one radio-frequency conductor to the other radio-frequency conductor. The directional coupler is therefore a directional coupler with a separated or divided substrate, wherein the radio-frequency conductors are movable relative to one another. The radio-frequency conductors are arranged and movable relative to one another such that the clearance (spacing) between the respective radio-frequency conductors remains constant, independent of the angle position of the parts of the rotating unit that are movable relative to one another. For example, such a clearance amounts to up to a few millimeters or a fraction thereof. At least one of the radio-frequency conductors of the directional coupler extends around the entire circumference of one of the two parts that are movable relative to one another, thus for example around the entire circumference of the rotor or around the entire circumference of the stator. The remaining radio-frequency conductor of the directional coupler is attached to the remaining part of the rotating unit, and in fact to at least a portion of the circumference of the remaining part. For example, a first radio-frequency conductor extends around the entire circumference of a rotor of a medical imaging device (in particular a computed tomography apparatus), and a second radio-frequency conductor is arranged on at least a portion of the circumference of a stator of a medical imaging device (in particular a computed tomography apparatus). In another example, a first radio-frequency conductor extends around the entire circumference of a stator of a medical imaging device (in particular a computed tomography apparatus), and a second radio-frequency conductor is arranged on at least a portion of the circumference of a rotor of a medical imaging device (in particular a computed tomography apparatus). In a further example, a first radio-frequency conductor extends around the entire circumference of a stator of a medical imaging device (in particular a computed tomography apparatus), and a second radio-frequency conductor extends around the entire circumference of a rotor of a medical imaging device (in particular a computed tomography apparatus), or vice versa.

In accordance with the invention the radio-frequency conductors of the directional coupler are always arranged identically relative to one another, independent of the angle position of the two parts that are movable relative to one another. The radio-frequency conductors are arranged among one another between the two parts that are movable relative to one another. Furthermore, the length of the radio-frequency conductor arranged at least partially around the circumference of one of the two parts amounts to a fraction of the circumference of the respective part, or to a fraction of the length of the radio-frequency conductor that is arranged on the entire circumference of the other part (for example one-third or one-fourth). This results in, with the second radio-frequency conductor (that is connected with the other communication device comprising at least one reception unit), a constant power from the radio-frequency conductor (which is connected with a communication device having at least one transmission unit) being transmitted wirelessly, and under constant conditions, from a first part to a second part of the rotating unit.

This also results in, with the second radio-frequency conductor that is connected with the communication device comprising at least one reception unit, a constant power being extracted from the radio-frequency conductor connected with the communication device having at least one transmission unit. Since the radio-frequency conductors of the directional coupler are located at two different parts of the rotating unit that are movable (in particular rotatable) relative to one another, this enables wireless data transmission within the rotating unit from one part to another part or, respectively, from the first communication device having a transmission unit to the second communication device having a reception unit. Furthermore, since the extracted power is constant along the longitudinal direction of the radio-frequency conductor that is connected with the communication device having a transmission unit, a signal (in particular a radio-frequency signal, especially a WLAN signal) can be transmitted with constant signal strength. A cancellation due to interferences and/or shielding is thereby avoided, and is in fact avoided independently of the respective position of the parts movable relative to one another, such that security-critical data can also be securely transmitted. Furthermore, since according to the invention the device for wireless data transmission has no antenna, it is not a radio-frequency transmission system. Complicated national and international radio approval processes thus do not apply. Therefore, a reliable, at least unidirectional radio-frequency data transmission with constant signal strength of measurement data (for example projection data for image reconstruction) and/or of operating data (control data, for example) between two parts of the rotating unit that are movable relative to one another is enabled.

The use of WLAN signals offers many advantages. Data transmissions via a wireless network with WLAN components is known in the home use field and in automation engineering. WLAN designates a standardized, wireless, local radio network in a frequency range from approximately 2 GHz to (presently) approximately 6 GHz. No interference with medical technology standards is thereby to be expected, for example. However, such transmission systems have an antenna, so these are radio-frequency transmission systems. In addition to an approval process for the medical field, the application of such a data transmission system would therefore also mean going through a complicated (and thus costly) national and/or international radio approval process. However, a WLAN signal is a radio-frequency signal and can transmit without an antenna in a rotating unit according to the invention with a device for wireless data transmission as already described above. One requirement for this is that the transmission unit of the first communication device or the reception unit of the second communication device be designed to provide and transmit or receive such WLAN signals. In the simplest case, this occurs by the at least one transmission unit of the first communication device or the at least one reception unit of the second communication device having at least one WLAN component or, expressed differently, are designed as a WLAN transmission unit or as a WLAN reception unit.

Such an embodiment of the rotating unit according to the invention offers many advantages. WLAN components or WLAN transmission units and/or WLAN reception units are available at a reasonable price, are widespread and widely tested. A data transmission capability is thereby achieved that is markedly cheaper than other proprietary solutions. Furthermore, a dependency on a single vendor is thereby avoided. Furthermore, the continuous development in the WLAN market ensures a continuous price decline given simultaneous increase of the data transfer rate. In addition to this, WLANs generally offer high data transfer rates of approximately 2 Mbits/s to 800 Mbits/s. WLAN is therefore sufficiently fast for control applications which require a transmission of operating data (in particular control data) in the range of approximately 20 Mbits/s. The transmission of measurement data (in particular of image data) is therefore also possible insofar as the image transfer rate is adapted to the data transfer rate of the WLAN. For example, this is the case if the image quality is low or is selected corresponding to the available data transfer rates. Such a transfer rate can in particular by all means be sufficient for simple devices with a limited image quality, or for image quality that is not selected to be too high. The development of additional standards with even higher transfer rates is moreover both possible and very probable in the future, such that it is to be expected that the available WLAN data transfer rates will increase even further. For example, a new standard is presently being developed which should enable data transfer rates up to 7 GB/s in the 60 GHz range. The transfer of image data of higher quality will be enabled in the future. Furthermore, WLAN has data security integrated into the transmission protocol; data security algorithms are thus already implemented, whereby the necessity to implement such data security algorithms in separate security-critical applications themselves, or by third parties, can no longer apply. Finally, the use of WLAN components is realistic with regard to signal attenuation and power losses, in particular because the output power of current WLAN components is sufficiently high in this context and delivers a sufficient signal (with approximately 100 mW and under consideration of conductor attenuation) to a WLAN receiver, in particular within a medical imaging device (for example a computer tomography apparatus).

In another embodiment of the invention, at least one of the radio-frequency conductors of the directional coupler is designed as a stripline conductor. Preferably both radio-frequency conductors are designed as stripline conductors. A stripline conductor is a waveguide that has at least one thin, conductive strip applied on or in a dielectric. Stripline conductors have the advantage that they are cost-effective to produce and can be produced with reproducible impedances (thus properties). They are additionally a widely tested, well-controlled technology. In the embodiment of at least one of the radio-frequency conductors of the directional coupler as a stripline conductor, a reliable, reproducible transmission is ensured. In addition, such stripline conductors can be produced in very thin and very narrow designs, such that they require little space overall and contribute little to the total weight of the rotating unit, which in particular is advantageous in many regards given a medical imaging device, especially in a computed tomography apparatus.

In a further embodiment of the invention, at least one of the communication devices is designed to provide a radio-frequency signal (in particular a WLAN signal) composed of at least two different frequencies or two different frequency ranges. For example, the first communication device that is connected with the actually terminated radio-frequency conductor is designed such that it provides a signal with at least two signal components of frequency f1 and f2 or at least two signal components in two different frequency ranges [f1, f1'] and [f2, f2']. For example, the second communication device is alternatively or additionally designed in a similar manner. The possibility is thereby achieved to feed at least two signals of different frequency in parallel into a radio-frequency conductor. The data transfer capacity is thereby at least doubled in one direction. The at least one of the communication devices is advantageously designed to provide a radio-frequency signal (in particular a WLAN signal) composed of more than two different frequencies or more than two different frequency ranges, whereby the transfer capacity is further increased in one direction.

The at least one communication device can have at least two different transmission units which are respectively designed to transmit a radio-frequency signal (in particular a WLAN signal) of a defined frequency fi or within a defined frequency range [fi, fi']. The at least one communication device advantageously has more than two different transmission units with these properties. The respective transmission units are advantageously switched in parallel with one another. The respective transmission units or the at least one communication device advantageously have at least one frequency-selective (preferably passive) filter. The transmission units are advantageously respectively designed with a (preferably passive) frequency-selective filter.

In another embodiment of the invention, at least one of the communication devices is designed for frequency-selective reception of a radio-frequency signal, in particular of a WLAN signal. The at least one communication device is designed for frequency-selective reception of at least two radio-frequency signals (in particular WLAN signals) of different frequencies f1 and f2 or different frequency ranges [f1, f1'] and [f2, f2']. It is thereby achieved that a radio-frequency signal (in particular a WLAN signal) with signal components of different frequency f1 and 12 or different frequency ranges [f1, f1'] and [f2, f2'] can be received in a frequency-dependent manner and be split up. It is thereby possible to split a signal having multiple frequency components into multiple individual signals of different frequency or frequency ranges, wherein a defined function or a defined component is associated with a signal of a defined frequency or a defined frequency range, for example. More data can thereby be transmitted and used via a single signal. The at least one of the communication devices for reception of a radio-frequency signal (in particular a WLAN signal) is designed for frequency-selective reception of a radio-frequency signal made up of more than two different frequencies or more than two different frequency ranges, so the transfer capacity is further increased in one direction.

The at least one communication device can have at least two different reception units which are respectively designed for frequency-selective reception of a radio-frequency signal (in particular a WLAN signal) of a defined frequency fi or a defined frequency range [fi, fi']. The at least one communication device advantageously has more than two different reception units with these properties. The respective reception units are switched in parallel with one another. The respective reception units (or the at least one communication device) have at least on frequency-selective (preferably passive) filter. The reception units are respectively designed with a (preferably passive) frequency-selective filter.

In another embodiment of the invention, the radio-frequency conductor that is connected at one side with the second communication device having at least one reception unit is likewise terminated at the other side by a real ohmic resistor, and both communication devices are designed as transmission/reception devices, i.e. each has at least one transmission unit and at least one reception unit. It is thereby achieved that a constant power can be extracted from one radio-frequency conductor with the other radio-frequency conductor. At the same time, it is also achieved that a constant power can be injected into the one radio-frequency conductor with the other radio-frequency conductor. Stated differently, both radio-frequency conductors thereby achieve the same capability of injection and/or extraction of a constant power into the other or from the other conductor. Since the radio-frequency conductors are located on two different parts of the rotating unit that are movable (in particular rotatable) relative to one another, this development enables a data exchange between the two parts movable relative to one another, for example thus between the rotor and the stator of a medical imaging device (a computer tomography apparatus, for example) or between the first communication device and the second communication device. Furthermore, since the extracted or injected power is constant along the longitudinal direction of the radio-frequency conductors, radio-frequency signals (in particular WLAN signals) with constant signal strength can be exchanged. Since—as before—no antenna is used, these does not involve a radio-frequency transmission system, so complicated national and international radio approval processes are unnecessary. Therefore, a reliable, bidirectional data transmission of a radio-frequency signal (in particular a WLAN signal) with constant signal strength—in particular of measurement data (for example projection data for image reconstruction) and/or operating data (for example control data) is enabled between the two parts of a rotating unit that are movable (advantageously rotatable) relative to one another. Furthermore, no second system, no additional communication device or additional radio-frequency conductor for data transmission in the second direction is necessary, so it is more cost-effective, easier and simpler to design in comparison to other solutions. Furthermore, this embodiment is even more advantageous if it is combined with communication devices that (as described in the preceding) provide at least one radio-frequency signal composed of different frequencies or frequency ranges and/or embody frequency-selective reception of at least one radio-frequency signal composed of different frequencies or frequency ranges.

In another embodiment of the invention each communication device has at least one transmission unit and at least one reception unit, and both radio-frequency conductors of the directional coupler are terminated with a real resistor. A data exchange can thereby take place between the communication devices in both directions. Furthermore, in this embodiment the respective transmission units of the respective communication devices transmit radio-frequency signals of different frequency or in different frequency ranges. This allows radio-frequency signals to be exchanged in both directions, and simultaneously between the communication devices by means of the same device for data transmission. Real-time communication is therefore achieved.

Furthermore, at least one communication device can have multiple transmission units to transmit a radio-frequency signal, in particular a WLAN signal. The transmission units of the communication device are each designed to transmit a radio-frequency signal of a defined frequency or in a defined frequency range. The respective transmission units of the communication device each have a (preferably passive) frequency-selective filter. Furthermore, the other communication device has multiple reception units for frequency-selective reception of a radio-frequency signal, in particular a WLAN signal. The reception units are each designed to receive a radio-frequency signal of a defined frequency or in a defined frequency range. The respective reception units are designed with a (preferably passive) frequency-selective filter for signal splitting. The respective transmission units and the respective reception units are switched in parallel with one another. The respective passive, frequency-selective filters of the individual transmission units and of the individual reception units have different properties; in particular, they can pass different frequencies or frequency ranges. The signal of multiple transmission units composed of different frequencies or different frequency ranges can be combined into a complete signal to be transmitted. A complete signal to be transmitted consequently has signal components of different frequencies, and can be extracted from one radio-frequency conductor via the other radio-frequency conductor and be subsequently split again (preferably depending on frequency) by the respective (preferably passive) frequency-selective filters of the individual reception units. At least a two-channel or multichannel capability is thereby enabled via only one transmission line. The signal combination takes place using frequency multiplexing. The available frequency band is thereby subdivided into different sub-bands, wherein a signal in a certain band is emphasized and is clearly detectable by the receiver due to its frequency position. There is thus necessarily a boundary band between two frequency sub-bands, i.e. a frequency range that is not used because frequency filters have only a finite gradient, and therefore only frequencies at defined intervals can be cleanly separated from one another. Overall, the transfer capacity between a first communication device and a second communication device can be multiplied without a modification of the transmission device being necessary. In addition, a radio-frequency signal in the other direction can simultaneously be transmitted via the same transmission device in real time insofar as the respective frequencies of the signals do not overlap. Both communication devices are preferably designed in this manner so that data exchange can take place in real time in both directions via multiple frequency channels and by means of the same device for data transmission. The transfer capacity is thereby maximized in both directions, and a bilateral real-time data exchange is enabled.

Furthermore, the present invention concerns a medical imaging device with a rotating unit according to the invention. The medical imaging device is preferably a computed tomography apparatus. The manufacturing costs of such a medical imaging device can be reduced by the solution for data transmission according to the invention, which is particularly advantageous for simpler apparatuses. In addition, the device for data transmission according to the invention contributes little to the total weight of the rotating unit, such that a medical imaging device having the rotating unit according to the invention will not become significantly heavier.

Furthermore, the present invention concerns a method for wireless transmission of measurement and/or operating data between a rotor and a stator of a medical imaging device (preferably a computed tomography apparatus). Such a method has at least the following steps: provide at least one radio-frequency signal to be transmitted between the rotor and the stator, and inject or extract at least a portion of the power of the provided radio-frequency signal, such that a constant power is injected or, respectively, extracted between the rotor and the stator. In particular, such a method according to the invention can be executed with a rotating unit according to the invention. With this method, an at least unilateral wireless data transmission is achieved that enables the transmission of security-critical data between a rotor and a stator of a medical imaging device (preferably a computed tomography apparatus).

In an embodiment of the method according to the invention, at least two radio-frequency signals are transmitted between the rotor and the stator such that a first radio-frequency signal to be transmitted is transmitted from the rotor to the stator, and a second radio-frequency signal to be transmitted is transmitted from the stator to the rotor. Data exchange is thereby enabled between the rotor and the stator of a medical imaging device (computed tomography apparatus). For example, status data of a component located at one of the parts can be queried, and control data can be sent back as a response. Therefore, a communication between the components of the rotating unit or the medical imaging device is thereby enabled.

In a further embodiment of the method according to the invention, first and second radio-frequency signals that are exchanged between the parts that are movable relative to one another have different frequencies, or have signal components composed of different frequency ranges, and the transmission of the respective signals between the parts that are movable relative to one another takes place simultaneously. A bilateral, simultaneous communication between the elements of the rotating unit or of the medical imaging device is thereby achieved.

In another embodiment of the method according to the invention, the at least one radio-frequency signal to be transmitted has at least two signal components in different frequency ranges or of different frequencies. An increase of the transfer capacity is thereby achieved in at least one transfer direction. This is preferably achieved in both directions, preferably in a bilateral, simultaneous communication, so the transfer capacity is multiplied.

In a further embodiment of the method according to the invention, the radio-frequency signal is a WLAN signal. Among other things, such a method has the advantage of having data security integrated into the transfer protocol, whereby data security algorithms are already implemented, such that the necessity of having data security algorithms implemented in separate, security-critical applications themselves, or by third parties, does not apply.

The advantages described for the rotating unit apply analogously to the medical imaging device and to the method.

DESCRIPTION OF THE PREFERRED EMBODIMENTS

Figure 1:
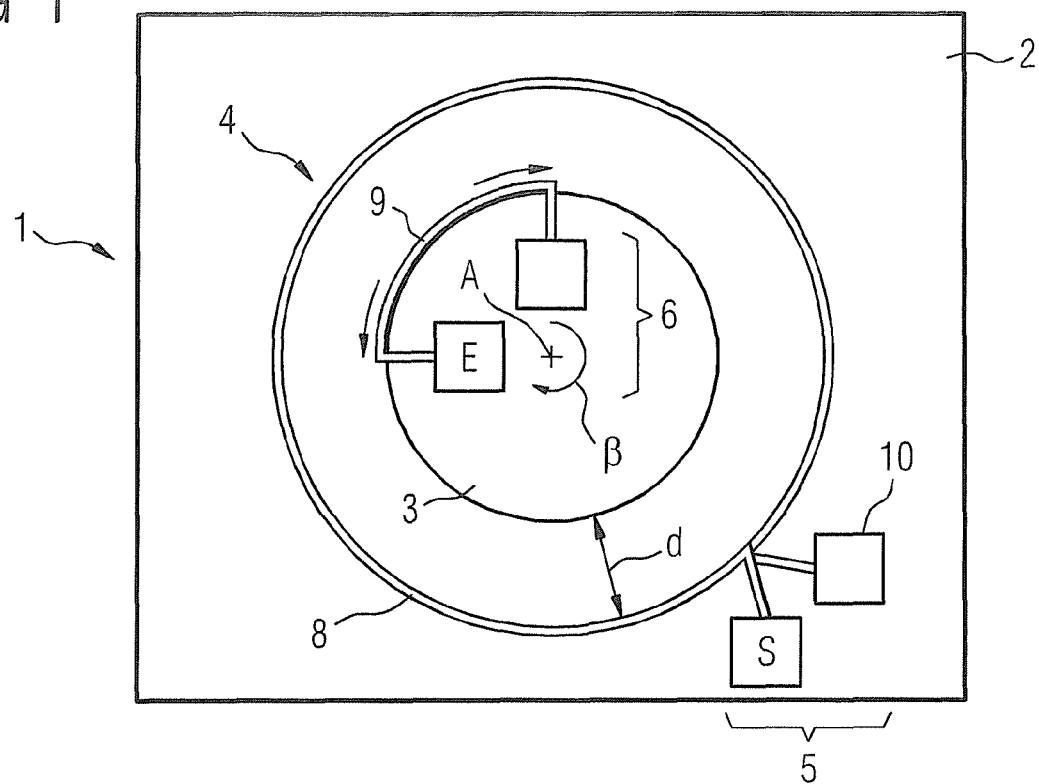
FIG. 1 is a schematic sectional view of a rotating unit according to the invention.

A rotating unit 1 according to the invention is schematically depicted in FIG. 1. The rotating unit 1 according to the invention has a stationary part 2 and a rotatable part 3 as well as a device 4 for wireless transmission of measurement data and/or operating data between the parts 2, 3. The device for wireless transmission 4 has a first communication device 5 and a second communication device 6, as well as a directional coupler 7. The directional coupler has two radio-frequency conductors 8 and 9. The first communication device 5 has at least one transmission unit S that is designed to output at least one radio-frequency signal (especially a WLAN signal). Furthermore, the second communication device 6 has at least one reception unit E that is designed to receive at least one radio-frequency signal (especially a WLAN signal). In this shown example, the first communication device 5 is arranged at the stationary part 2 of the rotating unit 1. In this shown example, the second communication device 6 is arranged at the rotatable part 3 of the rotating unit 1. Furthermore, one of the radio-frequency conductors 8 of the directional coupler is connected with the first communication device 5 and terminated with a real resistor 10. The second radio-frequency conductor 9 of the directional coupler is connected with the second communication device 6 of the device. Finally, in this shown example the first radio-frequency conductor 8 of the directional coupler that is connected with the first communication device 5 is arranged around the entire circumference of the stationary part 2 (preferably annularly). In this shown example, the second radio-frequency conductor 9 of the directional coupler is likewise arranged on the circumference of the rotatable part 3, but only on a portion of this. The clearance between the radio-frequency conductors 8, 9 is thereby constant at every angle position 13 of the rotatable part 2 around the rotation axis A of the rotating unit 1. A constant portion of the power of a signal induced by the transmission unit S in the first radio-frequency conductor thus can be extracted via the second radio-frequency conductor 9. A unilateral data transmission is thereby achieved between the first and second communication devices 5, 6, and thus between the stationary part 2 and the rotatable part 3.

In an example that is not shown, the first communication device 5 is arranged on the rotatable part 3 of the rotating unit and the second communication device 6 is arranged on the stationary part 2 of the rotating unit. In this example that is not shown, the first radio-frequency conductor 8 of the directional coupler which is connected with the first communication device 5 is arranged around the entire circumference of the rotatable part 3, while the second radio-frequency conductor 9 of the directional coupler is arranged only on a portion of the circumference of the stationary part 3. In a further example that is not shown, the first radio-frequency conductor 8 of the directional coupler which is connected with the first communication device 5 is arranged around the entire circumference of the rotatable part 3, while the second radio-frequency conductor 9 of the directional coupler is likewise arranged around the entire circumference of the stationary part 3.

Figure 2:
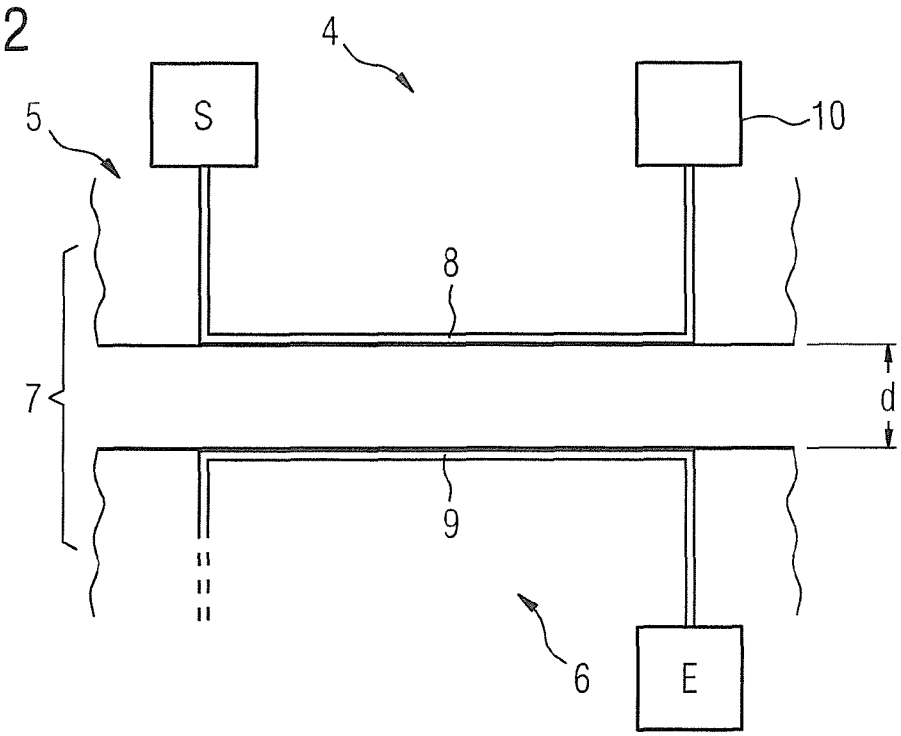
FIG. 2 is a schematic depiction of a device for wireless data transmission with which a unilateral transmission takes place between the parts of a rotating unit that are movable relative to one another.

FIG. 2 shows a schematic depiction of a device 4 for wireless data transmission with which a unilateral transmission can take place between the parts 2, 3 of a rotating unit 1 that are movable relative to one another. The device 4 is shown flat for simplification. The communication device 5 has at least one transmission unit S and, and a second communication device 6 has at least one reception unit E. The transmission unit S is connected with a radio-frequency conductor 8, which terminated with a real resistor 10. The reception unit E is connected with a second radio-frequency conductor 9. The radio-frequency conductors 8 and 9 are part of a directional coupler 7 with divided substrate. A constant signal is thereby generated along the radio-frequency conductor 8, from which a constant portion of the power can be extracted by means of the second radio-frequency conductor 9. A signal can therefore be transmitted from the transmission unit S to the reception unit E. The first and second communication devices are arranged on different parts 2, 3 of the rotating unit 1.

Figure 3:
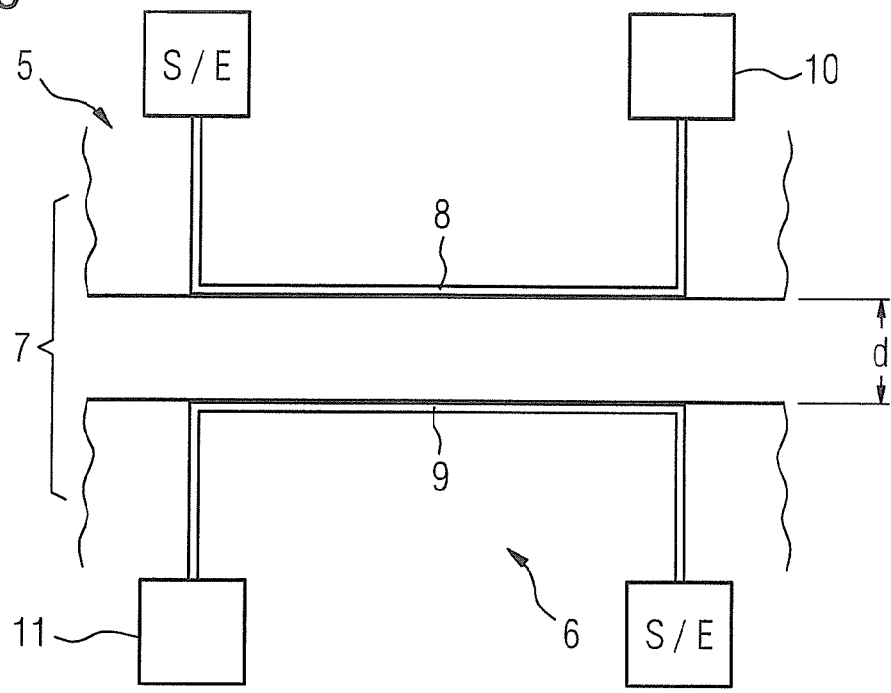
FIG. 3 is a schematic depiction of a device for wireless data transmission with which a bilateral transmission takes place between the parts of a rotating unit that are movable relative to one another.

FIG. 3 shows a schematic depiction of a device 4 for wireless data transmission with which a bilateral transmission can take place between the parts 2, 3 of a rotating unit 1 that are movable relative to one another. The device 4 is shown flat for simplification. Both communication devices 5, 6 thereby have at least one transmission unit S and one reception unit E. The radio-frequency conductors are also respectively terminated with real resistors 10, 11. Each communication device 5, 6 can both transmit and receive a radio-frequency signal. In that the second radio-frequency conductor 9 is likewise really terminated, a constant field likewise develops along this radio-frequency conductor 9, such that a constant power can likewise be injected and/or extracted from this radio-frequency conductor 9. Signals can therefore be transmitted from the transmission unit S to the reception unit E, and from the reception unit E to the transmission unit S. A bilateral data transmission is thereby enabled. The first and second communication devices are arranged at different parts 2, 3 of the rotating unit 1.

Figure 4:
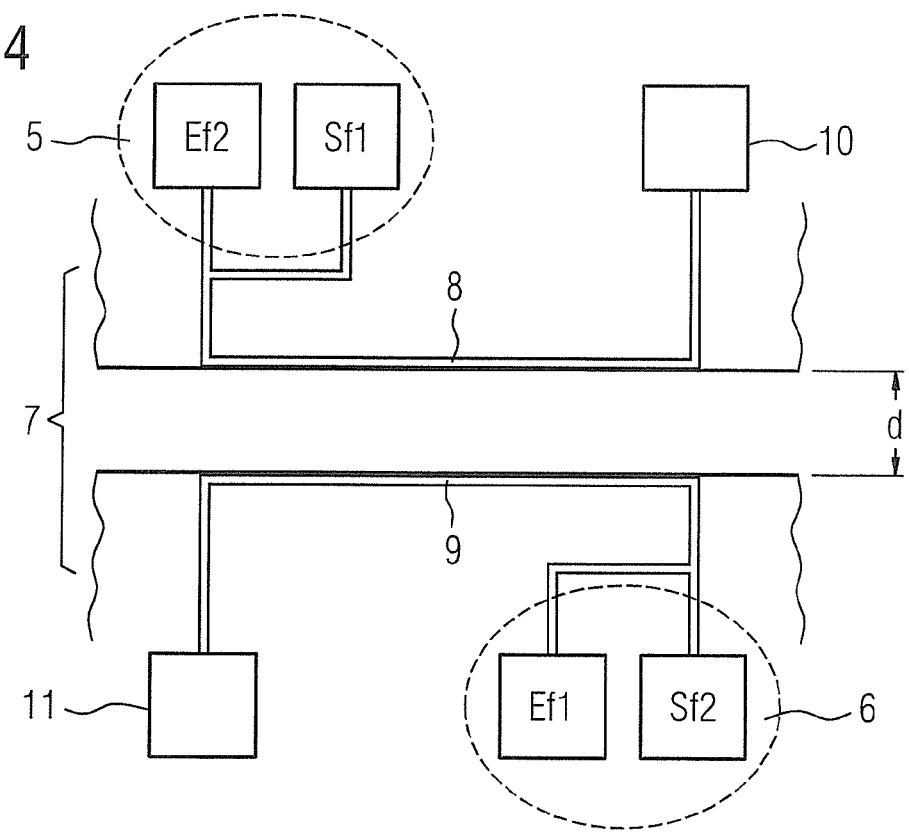
FIG. 4 is a schematic depiction of a device for wireless data transmission with which a simultaneous bilateral transmission takes place between the parts of a rotating unit that are movable relative to one another.

FIG. 4 shows a schematic depiction of a device 4 for wireless data transmission with which a simultaneous bilateral transmission is enabled between the parts 2, 3 of a rotating unit 1 that are movable relative to one another. Both communication devices 5, 6 have at least one transmission unit S and one reception unit E. In this example, the transmission unit Sf1 of the first communication device 5 is designed to transmit a radio-frequency signal of the frequency f1. The reception unit of the first communication device 5 is designed to receive a radio-frequency signal of a frequency f2. Furthermore, the transmission unit Sf2 of the second communication device 6 is designed to transmit a radio-frequency signal of a frequency f2, and the reception unit Ef1 of the second communication device 6 is designed to receive a radio-frequency signal of a frequency f1. Signals of different frequency f1, f2 can thus be induced and transmitted simultaneously by the radio-frequency conductors of the device 4, such that a simultaneous transmission of signals takes place from the transmission unit Sf1 to the reception unit Ef1, and simultaneously from the transmission unit Sf2 to the reception unit Ef2. A simultaneous bilateral data transmission thereby takes place. The first and second communication devices are arranged on different parts 2, 3 of the rotating unit 1.

In a further example (not shown), at least one of the communication devices 5, 6 has multiple transmission units Sfi that are each designed to transmit a radio-frequency signal of a frequency fi, and the other communication device has multiple reception units Efi which are each designed to receive a radio-frequency signal of a frequency fi. The transfer capacity can thereby be increased by means of the identical transmission conductor. In a further example that is not shown, both communication devices comprise multiple transmission units Sfi which are respectively designed to transmit a radio-frequency signal of a frequency fi, and multiple reception units Efi which are respectively designed to receive a radio-frequency signal of a frequency fi, wherein the transmission units of the respective communication devices transmit signals of different frequency. The transmission capacity can thereby be increased in both directions by a simultaneous bilateral data transmission.

In the aforementioned examples, the radio-frequency conductors are preferably designed as stripline conductors.

Although modifications and changes may be suggested by those skilled in the art, it is the intention of the inventor to embody within the patent warranted hereon all changes and modifications as reasonably and properly come within the scope of his contribution to the art.

I claim as my invention:

1. An imaging apparatus comprising:
   two parts, each having a circumference, that are rotatable relative to each other with respect to the respective circumferences thereof;
   a plurality of apparatus components mounted on said two parts that are collectively configured to generate image measurement data that are dependent on the rotation of the two parts relative to each other;
   a wireless transmission device configured to transmit at least one type of imaging data, selected from the group consisting of said imaging measurement data and imaging operating data, between said two parts;
   said wireless transmission device comprising a first communication device comprising at least one transmission unit, situated on a first of said two parts, that transmits at least one radio-frequency signal comprising said at least one type of data;

said wireless transmission device comprising a second communication device comprising at least one reception unit, situated on a second of said two parts, that receives said at least one radio-frequency signal; and a directional coupler comprising at least two radio-frequency conductors with a spacing there between that keeps said at least two radio-frequency conductors out of mechanical contact with each other during said rotation of said two parts, a first of said at least two radio-frequency conductors being connected at one end thereof with said first communication device and having an opposite end terminated with a real resistance, and a second of said at least two radio-frequency conductors being connected with said second communication device, said first and second of said at least two radio-frequency conductors being configured in a conductor configuration that causes a constant power to be extracted from said first of said radio-frequency conductors connected to said first communication device, said conductor configuration comprising said first of said at least two radio-frequency conductors extending annularly around an entirety of the circumference of said first of said two parts, and said second of said at least two radio-frequency conductors extending around at least a portion of the circumference of said second of said two parts.

2. An imaging apparatus as claimed in claim 1 wherein said at least one transmission unit is configured to transmit a WLAN signal as said at least one radio-frequency signal, and wherein said second communication device is configured to receive said WLAN signal.

3. An imaging apparatus as claimed in claim 1 wherein at least one of said at least two radio-frequency conductors is a stripline conductor.

4. An imaging apparatus as claimed in claim 1 wherein said first communication device is configured to transmit said at least one radio-frequency signal as a radio-frequency signal comprised of components having at least two different frequencies or frequency ranges, and wherein said at least one reception unit is configured to receive said at least one radio-frequency signal with signal components comprising said at least two different frequencies or frequency ranges.

5. An imaging apparatus as claimed in claim 4 wherein said first communication device is comprised of at least two different transmission units respectively configured to transmit different radio-frequency signals respectively having said at least two different frequencies or frequency ranges.

6. An imaging apparatus as claimed in claim 5 wherein said second communication device comprises two reception units respectively configured to receive said different radio-frequency signals having the respective different frequencies or frequency ranges.

7. An imaging apparatus as claimed in claim 1 wherein said second of said at least two radio-frequency conductors of said directional coupler is also terminated, at least at one and thereof, with a real resistance, and wherein said second communication device comprises a transmission unit configured to transmit at least one further radio-frequency signal and wherein said first communication device comprises a reception unit configured to receive said at least one further radio-frequency signal.

8. An imaging apparatus as claimed in claim 7 wherein the transmission unit of the first communication device transmits said radio-frequency signal at a first frequency or frequency range, and wherein said transmission unit of said second communication device transmits said further radio-frequency signal at a frequency or frequency range that is different from the frequency or frequency range of the radio-frequency signal transmitted by the transmission unit of said first communication device, and wherein the respective transmission units of the first communication device and the second communication device simultaneously transmit said radio-frequency signal and said further radio-frequency signal.

9. An imaging apparatus as claimed in claim 1 wherein said first communication device comprises multiple transmission units each comprising a passive, frequency-selective filter to respectively transmit a radio-frequency signal at a defined frequency or in a defined frequency range, and wherein said second communication device comprises multiple reception units, each configured for frequency-selective reception of the respective radio-frequency signals at said defined frequency or in said defined frequency range, transmitted by said multiple transmission units.

10. An imaging apparatus as claimed in claim 1 wherein at least one of said first communication device and said second communication device comprises at least one frequency-selective filter.

11. An imaging apparatus as claimed in claim 1 wherein said plurality of apparatus components are configured to generate computed tomography data as said image measurement data.

12. A method for operating a medical imaging apparatus in order to transmit measurement data between two parts, each having a circumference, that are rotatable relative to each other with respect to the respective circumferences thereof, said method comprising:

collectively using a plurality of apparatus components mounted on said two parts to generate image measurement data that are dependent on the rotation of the two parts relative to each other;

wirelessly transmitting at least one type of imaging data, selected from the group consisting of said imaging measurement data and imaging operating data, between a first communication device comprising at least one transmission unit, situated on a first of said two parts, that transmits at least one radio-frequency signal comprising said at least one type of data, and a second communication device comprising at least one reception unit, situated on a second of said two parts, that receives said at least one radio-frequency signal;

providing a directional coupler comprising at least two radio-frequency conductors with a spacing there between that keeps said at least two radio-frequency conductors out of mechanical contact with each other during said rotation of said two parts, and connecting a first of said at least two radio-frequency conductors at one end thereof with said first communication device and terminating an opposite end of said first of said at least two radio-frequency conductors with a real resistance, and connecting a second of said at least two radio-frequency conductors with said second communication device, and configuring said first and second of said at least two radio-frequency conductors in a conductor configuration that causes a constant power to be extracted from said first of said radio-frequency conductors connected to said first communication device, by extending said first of said at least two radio-frequency conductors annularly around an entirety of the circumference of said first of said two parts, and extending said second of said at least two radio-frequency conductors around at least a portion of the circumference of said second of said two parts.

13. A method as claimed in claim 12 comprising transmitting at least two radio-frequency signals between said rotor and said stator, with a first of said at least two radio-frequency signals being transmitted from the rotor to the stator and a second of said at least two radio-frequency signals being transmitted from the stator to the rotor.

14. A method as claimed in claim 13 wherein said at least two radio-frequency signals have respectively different frequencies or frequency ranges, and are transmitted simultaneously.

15. A method as claimed in claim 12 wherein at least one of said at least two radio-frequency signals comprises at least two signal components of respectively different frequencies or frequency ranges.

16. A method as claimed in claim 12 comprising transmitting said radio-frequency signal as a WLAN signal.

\* \* \* \* \*